US012186068B2

(12) United States Patent
Weiss et al.

(10) Patent No.: US 12,186,068 B2
(45) Date of Patent: Jan. 7, 2025

(54) EAR PROTECTION FOR MEDICAL IMAGING

(71) Applicant: KONINKLIJKE PHILIPS N.V., Eindhoven (NL)

(72) Inventors: Steffen Weiss, Hamburg (DE); Mark Thomas Johnson, Arendonk (BE)

(73) Assignee: Koninklijke Philips N.V., Eindhoven (NL)

( * ) Notice: Subject to any disclaimer, the term of this patent is extended or adjusted under 35 U.S.C. 154(b) by 222 days.

(21) Appl. No.: 17/925,951

(22) PCT Filed: May 12, 2021

(86) PCT No.: PCT/EP2021/062563
§ 371 (c)(1),
(2) Date: Nov. 17, 2022

(87) PCT Pub. No.: WO2021/233747
PCT Pub. Date: Nov. 25, 2021

(65) Prior Publication Data
US 2023/0172480 A1 Jun. 8, 2023

(30) Foreign Application Priority Data
May 18, 2020 (EP) .................................... 20175173

(51) Int. Cl.
*A61B 5/055* (2006.01)
*A61F 11/08* (2006.01)
*A61F 11/14* (2006.01)

(52) U.S. Cl.
CPC .............. *A61B 5/055* (2013.01); *A61F 11/08* (2013.01); *A61F 11/14* (2013.01)

(58) Field of Classification Search
CPC .......... A61B 5/055; A61F 11/08; A61F 11/14; G01R 33/283; G01R 33/288; G10K 11/16
See application file for complete search history.

(56) References Cited

U.S. PATENT DOCUMENTS

| 2002/0076057 A1 | 6/2002 | Voix |
| 2004/0086138 A1 | 5/2004 | Kuth |

(Continued)

FOREIGN PATENT DOCUMENTS

| GB | 2519976 A | 5/2015 |
| WO | 2020234013 A1 | 11/2020 |

OTHER PUBLICATIONS

Moelker A et al. Importance of Bone-Conducted Sound Transmission on Patient Hearing in the MR Scanner. J Magn Reson Imag 2005;22:163-169.

(Continued)

*Primary Examiner* — Kile O Blair

(57) ABSTRACT

The present disclosure relates to an ear protection system (200) for a medical imaging device. It comprises an ear protection device (210), adapted to be fitted around or in the ears of a patient (P) to be imaged, and at least comprising a first communication interface (211) and at least one sensor device (212) adapted to determine a measurement of noise passing through the ear protection device (210) towards the ears of the patient. The system (200) further comprises a controllable signal emitter (230), adapted to output a proxy signal representing an expected imaging device noise and to be measured by the at least one sensor device (212), and a patient assistance device (220), adapted to assist the patient to fit the ear protection device (210), and at least comprising a second communication interface. During a preparation phase of the patient preceding an imaging phase using the medical imaging device, the ear protection device (210) and the patient assistance device (220) are communicatively connected to each other via the first and second communication interface, and the patient assistance device (220) generates assisting instructions to the patient depending on an evaluation of the proxy signal and the measurement of (Continued)

noise passing through the ear protection device (210) determined by the sensor device (212).

15 Claims, 3 Drawing Sheets

(56) References Cited

U.S. PATENT DOCUMENTS

| | | |
|---|---|---|
| 2013/0094658 A1 | 4/2013 | Holter |
| 2014/0012127 A1 | 1/2014 | Biber et al. |
| 2015/0010158 A1* | 1/2015 | Broadley ................ A61F 11/14 381/58 |

OTHER PUBLICATIONS

Trompette et al "Suitability of Commercially Available Systems for Individual Fit Tests of Hearing Protectors" Internoise 2013.
International Search Report and Written Opinion from PCT/EP2021/062563 mailed Aug. 2, 2021.

* cited by examiner

EAR PROTECTION FOR MEDICAL IMAGING

CROSS REFERENCE TO RELATED APPLICATIONS

This application is a U.S. national phase application of International Application No. PCT/EP2021/062563 filed May 12, 2021, which claims the benefit of EP application Ser. No. 20/175,173.2 filed on May 18, 2020 and is incorporated herein by reference.

FIELD OF THE INVENTION

The present invention relates to an ear protection system for a medical imaging device, a medical imaging system, a method of ear protection in medical imaging, a computer program element and a computer readable medium.

BACKGROUND OF THE INVENTION

Patients undergoing Magnetic Resonance Imaging (MRI) are routinely subjected to high sound pressure levels, averaging around 95-105 dB, and for some MR pulse sequences this can increase up to 130 dB and even beyond (Moelker A et al. Importance of Bone-Conducted Sound Transmission on Patient Hearing in the MR Scanner. J Magn Reson Imag 2005;22:163-169). Therefore, the wearing of ear protection is mandatory during MR exams, and different sorts of ear protection are used, mostly in the form of ear muffs and in-ear foam plugs as shown in FIG. 3. Ear muffs are more widely used, because they can be applied more easily and quickly, and because ear plugs are inconvenient for many patients and may not be applied properly by children, elderly, or demented patients.

The efficiency of protection depends critically on their correct application, but patients are often not used to wearing such ear protection, or are incapable of applying them properly. Consequently, studies have shown that the actual attenuation of sound for patients is 5 dB to 25 dB lower than the rated attenuation when devices are applied by normal users (Trompette N, Kusy A. Suitability of Commercially Available Systems for Individual Fit Tests of Hearing Protectors. Internoise 2013, Innsbruck). The reason for this difference is mainly incorrect application by the end user. This results in a general problem in MR, because most patients are not used to apply ear protection. Patients lack experience of what the correct level of attenuation should be and are not aware that they may be experiencing excessive noise levels, and there are no objective measures to check proper attenuation in-situ. Thus, there is no objective measure to check whether ear muffs or plugs have been applied properly, rather sometimes a subjective check is performed in which the radiographer asks the patient during patient preparation, whether the devices fit tightly. Ear muffs have to be applied such that there is no break or opening in the seal around the ear.

Therefore, there may be a need to assist the patient in applying ear protection during patient preparation.

SUMMARY OF THE INVENTION

It would be advantageous to have improved means of providing ear protection during medical examination by a medical imaging device, such as an MR imaging device. The object of the present invention is solved by the subject-matter of the independent claims, wherein further embodiments are incorporated in the dependent claims.

According to a first aspect, there is provided an ear protection system for a medical imaging device. The ear protection system comprises:

an ear protection device, adapted to be fitted around or in the ears of a patient to be imaged, and at least comprising a first communication interface and at least one sensor device adapted to determine a measurement of noise passing through the ear protection device towards the ears of the patient, a controllable signal emitter, adapted to output a proxy signal representing an expected imaging device noise, and to be measured by the at least one sensor device, a patient assistance device, adapted to assist the patient to fit the ear protection device, and at least comprising a second communication interface, wherein, during a preparation phase of the patient preceding an imaging phase using the medical imaging device, the ear protection device and the patient assistance device are communicatively connected to each other via the first and second communication interface, and the patient assistance device generates assisting instructions to the patient depending on an evaluation of the generated noise and the measurement of noise passing through the ear protection device determined by the sensor device.

In this way an ear protection system is provided to protect a patient during the imaging phase, such as Magnetic Resonance imaging MRI, where noise levels typically are around 95 to 105 dB and can be 130 dB and above. The wearing of ear protectors is mandatory for an MRI examination, however patients are generally not used to wearing such protection and consequently may not wear the ear protectors appropriately for the required level of protection, a situation exacerbated for children, elderly and patients with dementia. The provided system addresses this through e.g. monitoring the effectiveness of the protection being provided by the ear protection device, and giving supporting instructions to the patient. A workflow implemented with the above ear protection system supports at least semi-autonomous medical imaging.

The ear protection system may optionally be a part of or may be integrated into a medical imaging device and/or a medical imaging system.

The above systems and/or devices may be at least partially computer-implemented and may comprise one or more of a data processing device, i.e. a processor, a memory, one or more suitable data and/or communication interfaces, or the like. The functionalities and/or method steps described herein may be implemented in hardware, software or a combination thereof.

The ear protection device may comprise one or more of a pair of ear muffs, ear plugs, or the like.

The first and/or second communication interface may be broadly understood, and may comprise one or more of a wired communication technique, a wireless communication technique, etc. Preferably, the first and/or second communication interface is a wireless device or module, such as a Bluetooth device or module, a Wireless Local Area Network device or module, or the like, so that, for example, the patient can move as freely as possible and, if necessary, carry the ear protection device from a first location where the preparation phase is carried out to a second location where the imaging phase is carried out without having to remove the ear protection device and without interrupting a communication link. By way of example, the first location may be a preparation room and the second location may be an examination room where the medical imaging device is located.

The ear protection system may further be adapted to provide a measurement of effectiveness of fit of the ear protection device at the patient.

The at least one sensor device may comprise one or more of an optical sensor arrangement, an acoustic sensor arrangement, such as one or more microphones etc., a pressure measuring arrangement, an electrical measurement arrangement, which may also be combined. In an example, the at least one sensor device may comprise at least one microphone. The measurement of effectiveness of fit of the pair of ear muffs around the ears of the patient comprises at least one measured sound level. In an example, the at least one sensor device comprises a pair of air tubes. A first air tube of the pair of air tubes connects an inner chamber of a first ear muff that is configured to surround a first ear of the patient to the at least one microphone. A second air tube of the pair of air tubes connects an inner chamber of a second ear muff that is configured to surround a second ear of the patient to the at least one microphone.

In other words, air tubes connect the inner portion of the ear muffs, to detect the level of noise to which the patient's ears are being subjected, to microphones that are external to the ear muffs, for example integrated into an in-room operating console of an MRI system, or integrated with the MRI head coil, or integrated with the patient support for example. In this manner, the wired microphones are at a safe distance from the patient and are safely outside of the imaging region of the MRI system, whilst passive air tubes are in that region transferring the level of sound at the patient's ears to these external microphones, where that level of sound indicates the effectiveness of fit of the ear protection device. Thus, an preferably automated ear protection system can be provided, where the actual level of sound the patient is being subjected to is monitored. In some embodiments, this is used in order to automatically adjust the compression of ear protection device until the required level of attenuation is provided, and where the patient and/or device operator can be involved in this process through being able to manually change the level of compression for example.

Thus, the sound level is measured after attenuation by additional microphones. However, rather than the integration of such microphones into the ear muffs, which is prohibitive for RF safety reasons, air tubes are used for connection between the muffs and microphones that are external to the ear muffs, for example integrated in the MR head coil.

In an example, the at least one sensor device comprises a pair of photosensitive devices. A first photosensitive device of the pair of photosensitive devices is located with respect to a seal around an inner chamber of a first ear muff that is configured to surround a first ear of the patient. The first photosensitive device is located to detect light leakage past the seal. A second photosensitive device of the pair of photosensitive devices is located with respect to a seal around an inner chamber of a second ear muff that is configured to surround a second ear of the patient. The second photosensitive device is located to detect light leakage past the seal. The measurement of effectiveness of fit of the pair of ear muffs around the ears of the patient comprises at least one measured light level.

In other words, a "proxy" noise detection system is provided to determine the effectiveness of fit of the ear protection device, where a light leakage approach is used.

Thus, in an example for a non-transparent pair of ear muffs, a photosensitive device such as a photodiode is used inside the ear muff, and any light leaking into the ear muff is detected by the photodiode and is a direct indicator of the effectiveness of the fit of the ear muffs, and a level of compression can be applied to provide the required level of seal around the ear muffs to provide the required level of ear protection. Or, in another example a light source is provided inside the ear muffs and a photosensitive device is positioned outside the ear muff, and any light leaking from inside to outside is a direct indicator of the effectiveness of the fit of the ear muffs, and a level of compression can be applied to provide the required level of seal around the ear muffs to provide the required level of ear protection. Thus, in this example the system becomes independent of the light level, and can operate when there is no ambient lighting. Additionally, in an example the light source can be infrared in order to differentiate from ambient lighting and/or be modulated in a known way in order that the light from the photodiode can be detected even when there is ambient lighting.

In an example, the at least one sensor device comprises a pair of gas pressure sensors. A first gas pressure sensor of the pair of gas pressure sensors is located within an inner chamber of a first ear muff that is configured to surround a first ear of the patient. A second gas pressure sensor of the pair of gas pressure sensors is located within an inner chamber of a second ear muff that is configured to surround a second ear of the patient. The measurement of effectiveness of fit of the pair of ear muffs around the ears of the patient comprises at least one measured gas pressure level.

In other words, a "proxy" noise detection system is provided to determine the effectiveness of fit of the ear protectors, where a slight positive or negative pressure differential between the inside of the ear muff and the outside can be used to provide a direct indicator of the effectiveness of the fit of the ear muffs, and a proxy indicator of the noise attenuation is provided, and a level of compression can be applied to provide the required level of seal around the ear muffs to provide the required level of ear protection. Thus, an automated ear protection system can be provided, where a proxy indicator is used to measure the level of sound the patient is being subjected to and directly measure an effectiveness of fit of the ear muffs based on pressure signals in order to automatically adjust the compression of ear protectors until the required level of attenuation is provided, and where the patient and/or device operator can be involved in this process through being able to manually change the level of compression for example.

In an example, the at least one sensor device comprises a pair of electrodes. A first electrode of the pair of electrodes is located at a periphery of a first ear muff such that when the first ear muff is positioned to surround a first ear of the patient the first electrode is configured to contact and/or be adjacent to skin of the patient. A second electrode of the pair of electrodes is located at a periphery of a second ear muff such that when the second ear muff is positioned to surround a second ear of the patient the second electrode is configured to contact and/or be adjacent to skin of the patient. The measurement of effectiveness of fit of the pair of ear muffs around the ears of the patient comprises at least one impedance, conductance, or capacitance level.

In other words, a "proxy" noise detection system is provided to determine the effectiveness of fit of the ear protectors, where a number of different electrical approaches can be used. Thus, electrical monitoring using appropriate sensors on the seal position of the ear muffs is used to measure impedance, conductance or capacitance, and is a direct indicator of the effectiveness of the fit of the ear muffs, a proxy indicator of the noise attenuation being provided, and a level of compression can be applied to provide the required level of seal around the ear muffs to provide the required level of ear protection. Thus, an automated ear protection system can be provided, where a proxy indicator is used to measure the level of sound the patient is being subjected to and directly measure an effectiveness of fit of the ear muffs based on electrical signals in order to automatically adjust the compression of ear protectors until the required level of attenuation is provided, and where the patient and/or device operator can be involved in this process through being able to manually change the level of compression for example.

In other words, a measurement with one electrode associated with an ear muff can be used to determine how tight that ear muff is around the ear. The electrode associated with the other ear muff can similarly be used to determine how tight that ear muff is around the ear.

Thus, one electrode can be used to determine an effectiveness of fit, for example against ground level. However, in an example two or more electrodes can be used around the periphery or seal of each ear muff, and impedance, conductance or capacitance can be measured between adjacent electrodes to determine an effectiveness or tightness of fit. Indeed, electrodes can be spaced all around the seal of each ear muff and when in contact with the skin of the patient impedance, conductance or capacitance can be measured between adjacent electrodes to determine an effectiveness or tightness of fit.

The patient assistance device may be further adapted to provide the instructions to the patient by using one or more representation, communication and/or user interaction techniques. For example, the patient assistance device may be adapted to represent the instructions to the patient and/or communicate with the patient in visual, audio, etc. Further, the patient assistance device may be adapted to generate these instructions automatically.

The controllable signal emitter is adapted to output a proxy signal representing an expected imaging device noise and/or enabling a measurement of attenuation, to be measured by the at least one sensor device. In general, there is no need to measure directly a sound or noise level, but it can be replaced or represented by the proxy signal and use of a suitable proxy measuring method as explained herein. Thus, an, preferably automated, ear protection system can be provided, where the proxy signal is used as a proxy indicator to measure the level of sound the patient is being subjected to and directly measure an effectiveness of fit of the ear muffs based on monitoring the proxy signal, e.g. by light monitoring, pressure monitoring, or the like. The signal emitter may comprise one or more of at least one loudspeaker to emit a sound-based or noise-based signal, sound etc., playback data containing e.g. a recording of medical imaging device typical noise, an electronic or software-based noise generator, at least one light emitter to emit a light-based signal, a pressure generator to generate a slight constant positive or negative air pressure within the ear muff to be used as the proxy signal, an or the like. Note that the imaging device typical noise may also be the actual noises produced by the imaging devices themselves. However, other noises may fall into same category; namely sounds with frequency spectra which are highly suitable for checking the quality of the acoustic protection provided by the ear protection device without actually mimicking the actual sounds produced by the imaging device. By way of example, the signal emitter may provide e.g. (white) noise spectra at specific intensities, spectra containing single or multiple frequency peaks in the range produced by the actual devices etc. Further, there may be other suitable test frequency spectra to assess different causes for the insufficient acoustic protection (e.g. high frequencies can penetrate through small gaps, whereas lower frequencies can do so less well. It is noted that the signal emitter may be arranged externally to the ear protection device or may be a structural part of the ear protection device. As used herein, the proxy signal generated by the signal emitter may also be referred to as a reference signal that enables measurement of attenuation of the ear protection device.

The preparation phase precedes the imaging phase in a timely manner, so that the preparation phase is preferably completed before the imaging phase is initiated. Further, the preparation phase may optionally be carried out at a first location that is spaced apart from a second location where the imaging phase may be carried out. Optionally, the first and second location may be physically separated from each other.

The evaluation of the generated noise and the measurement of noise passing through the ear protection device determined by the sensor device may be carried out by a suitable data processing device, which may be adapted to execute a suitable software or the like.

According to an embodiment, a transition from the preparation phase to the imaging phase may be, preferably electronically, controlled depending on the evaluation result. For example, the ear protection systems may be adapted to provide a signal indicative of whether or not the preparation phase has been successfully completed, with the transition to the imaging phase being e.g. suspended, cancelled, or the like, if not successfully completed. This can further improve the level of automation in medical imaging. In addition, patient safety can be increased, since the imaging phase can only be released or enabled and, optionally, initiated afterwards, if the ear protection is sufficiently effective.

In an embodiment, the patient assistance device may further be adapted to repeat the evaluation when it is determined based on the evaluation result that the noise being passed through reaches or exceeds a certain threshold, e.g. a noise protection limit or the like, and to adapt the instructions to the evaluation result if necessary. In other words, the evaluation can be done iteratively. The generated instructions may differ from iteration step to iteration step, depending on the reason or cause why the noise passed through (still) reaches or exceeds the certain threshold. The certain threshold may be set to comply with noise regulations for medical imaging. This can further increase the effectiveness of the ear protection.

According to an embodiment, the ear protection system may further comprise an actuator adapted to adjust the fit of the ear protection device around the ears of the patient by applying a compression force that acts between the ear protection device and the patient, wherein the patient assistant device may further be adapted to generate instructions regarding the operation of the actuator. For example, a data processing device may be configured to control the actuator to adjust the fit of the pair of ear muffs around the ears of the patient, the control comprising utilization of the measurement of effectiveness of fit of the ear protection device. In at least some embodiments, the actuator may be configured as a pneumatic system that is adapted to adjust the compression until a correctly tight seal is provided around the ear protection device and thus sufficient attenuation of sound is obtained. Also, because the correct level of compression is enabled to be provided, the ear protection device that mitigation of the provision of ear protectors that are too tightly compressed against the head is provided. In other words, the system results in generally lower levels of compression, increasing the comfort to the patient during long scans.

In an embodiment, the ear protection system and/or the patient assistant device may further be adapted to electronically control a passage blocking device arranged between a first location where the preparation phase is carried out and a second location where the imaging phase using the medical imaging device is carried out, wherein the passage blocking device is controlled to be released for the patient to pass when the evaluation result indicates that a level of the noise passing through the ear protection device is below a certain threshold. In at least some embodiments, the passage blocking device may comprise a physical device, preferably a motor-driven door. Further, in at least some embodiments, the passage blocking device may comprise a traffic light or other visual means adapted to indicate at least visually whether or not the patient is to pass. This allows an even higher degree of automation in medical imaging because the patient is guided continuously, at least until reaching the medical imaging device for undergoing the imaging phase, or even during the imaging phase.

According to an embodiment, the ear protection system and/or the ear protection device may further comprise at least one audio output device adapted to provide the instructions of the patient assistant device to the patient in audio. For example, the system or device may generate voice instructions to be output by the audio output device. In at least some embodiments, the audio output device may be an outside audio output device arranged at the ear protection device to provide sound to the surroundings of the ear protection device. This allows for giving the instructions or guidance in a phase where the patient has not yet fitted or not yet correctly fitted the ear protection device. Further, in at least some embodiments, the audio output device may be an internal audio output device arranged at the ear protection device to provide sound to the patient's ear when the ear protection device is fitted to the patient. This allows for giving the instructions during each phase, namely during the preparation phase and/or the imaging phase, by using the ear protection device itself. For example, the audio output device may be formed by or may comprise at least one loudspeaker, or the like. Additionally or alternatively, the ear protection system may further comprise at least one graphical output device adapted to provide the instructions of the patient assistant device to the patient visually. For example, the graphical output device may comprise one or more of a display, a video screen, or the like.

For example, the ear protection system may comprise a data processing device, one or more of a video screen and an audio output device at the first location where the preparation phase is carried out, such as a preparation room. The ear protection system may utilize the graphical output device and/or the audio output device to introduce the function of the ear protection device to the patient. The ear protection system may instruct or ask the patient to put on or fit the ear protection device. For example, the audio output device may produce e.g. MR noise, i.e. a reference sound, and the ear protection system measures the residual sound inside the ear protection device to check for sufficient protection. If this is not the case, the ear protection system may instruct or ask the patient to reposition/adjust the ear protection device and rechecks, e.g. until sufficient noise suppression is achieved. By way of example, the generated instructions may provide an introduction to the ear protection device, such as: "Dear Patient, I am your ear protection device. I will now show you how to apply me properly so that you can listen to your favorite music during MR scanning without being disturbed by MR noise. Please, apply me to your ears as shown on the screen . . . ". Accordingly, the ear protection system may also be adapted to generate background sounds, such as music.

In an embodiment, the ear protection system may further comprise a natural language processing, NLP, engine adapted to affect the generation of the instructions at least based on the measurement of noise passing through the ear protection device determined by the sensor device. For example, this may improve autonomous imaging situations where only few or no staff is available for giving instructions to the patient. The NLP engine may comprise one or more of aspects of Natural Language Understanding (NLU), Natural Language Generation (NLG) and Dialogue Management (DM).

In an example where the at least one sensor device comprises at least one microphone inside the ear protection device, and the patient is subjected to the reference sound of the MRI, the NLP may be controlled and/or instructed to issue a verbal instruction that the ear protection device is correctly positioned, if the reference sound level recorded by the microphone is below a certain threshold. Optionally, the NLP may instruct the patient to proceed to the medical imaging device, e.g. to the second location.

In an example where the reference sound level recorded by the microphone is above a certain threshold, the NLP engine may be controlled and/or instructed to issue a verbal instruction that the protection is not yet correctly positioned. Optionally, the NLP may instruct the patient to adjust the positioning of the ear protection device.

In an example where the reference sound level recorded by the microphone in one ear is above a certain threshold and in the other ear the microphone sound level is below a certain threshold issue a verbal instruction that the protection is not yet correctly positioned on e.g. one ear or both ears, etc. Optionally, the NLP engine may instruct the patient to adjust the positioning of the headphones on that ear.

It is noted that the above may be carried out by using other sensor technologies, such as an optical sensor, where the NLP engine may be driven by the relationship of a light intensity to a certain light intensity threshold.

Further, the NLP engine may utilize Natural Language Understanding (NLU), adapted to understand questions or comments that the patient may make. For this purpose, the ear protection system may comprise an audio input device, such as a microphone.

Further, optionally, the NLP engine may utilize Natural Language Generation (NLG), adapted to generate responses to the patient based on e.g. the patient's actions and requirements. This allows communication with the patient to be particularly well adapted to the respective situation.

According to an embodiment, the ear protection system may further comprise at least one microphone adapted to record or capture the voice of the patient and/or the generated noise, wherein the NLP engine may further be adapted to at least semi-automatically generate the instructions to the patient in speech based on the recording or capture from the microphone.

In an embodiment, the ear protection system may further comprise at least two of the sensor devices adapted to determine a measurement of noise passing through the ear protection device towards the ears of the patient, wherein at least one of the sensor devices is assigned to a first ear and at least one other of the sensor devices is assigned to a second ear of the patient. This allows side-specific instructions to be generated, so that e.g. positioning or repositioning of the ear protection device may be further facilitated.

According to a first aspect, there is provided a medical imaging system. The system comprises:
a medical imaging device, and
an ear protection system, comprising:
an ear protection device, adapted to fit around the ears of a patient to be imaged, and at least comprising a first communication interface and a sensor device adapted to determine a measurement of noise passing through the ear protection device towards the ears of the patient,
a patient assistance device, adapted to assist the patient, by using instructions, to fit the ear protection device around its ears, and at least comprising a second communication interface and a controllable signal emitter, adapted to output a proxy signal representing an expected imaging device noise and to be measured by the at least one sensor device,
wherein, during a preparation phase of the patient preceding an imaging phase using the medical imaging device, the ear protection device and the patient assistance device are communicatively connected to each other via the first and second communication interface, and the patient assistance device generates instructions to the patient depending on an evaluation of the generated noise and the measurement of noise passing through the ear protection device determined by the sensor device.

In this way an ear protection system is provided to protect a patient during the imaging phase, such as Magnetic Resonance imaging MRI, where noise levels typically are around 95 to 105 dB and can be 130 dB and above. The wearing of ear protectors is mandatory for an MRI examination, however patients are generally not used to wearing such protection and consequently may not wear the ear protectors appropriately for the required level of protection, a situation exacerbated for children, elderly and patients with dementia. The provided system addresses this through e.g. monitoring the effectiveness of the protection being provided by the ear protection device, and giving supporting instructions to the patient. A workflow implemented with the above ear protection system supports at least semi-autonomous medical imaging.

Preferably, the medical imaging device is an MR imaging device.

In at least some embodiments, the ear protection system and the medical imaging device may be communicatively connected to each other, e.g. via a suitable communication interface, so that the ear protection system may at least partially control the medical imaging device, and vice versa.

According to an embodiment, a transition from the preparation phase to the imaging phase may be, preferably electronically, controlled depending on the evaluation result.

In an embodiment, during the imaging phase, the noise passing through the ear protection device may be monitored and evaluated, and, when the evaluation indicates that a level of the noise passing through the ear protection device reaches or exceeds a certain threshold, the imaging phase may be at least interrupted automatically by controlling the medical imaging device. In other words, noise suppression may be monitored, e.g. continuously, during the imaging phase, such as MR scanning. If the residual noise level for the patient reaches or exceeds a certain threshold level that could lead to hearing damage for the patient, the imaging, e.g. MR scanning, may be stopped automatically. This can further improve patient safety.

According to a second aspect, there is provided a, preferably computer-implemented, method of ear protection in medical imaging. Optionally, the method may be carried out by using the ear protection system according to the first aspect and/or the medical imaging system according to the second aspect. The method comprises the steps of:
providing an ear protection device, adapted to be fitted around or in the ears, to a patient to be imaged,
generating, by a controllable signal emitter, during a preparation phase of the patient preceding an imaging phase, a proxy signal representing an expected imaging device noise and to be measured by the at least one sensor device,
determining, by at least one sensor device, a measurement of noise passing through the ear protection device towards the ears of the patient,
generating assisting instructions to the patient depending on an evaluation of the generated noise and the measurement of noise passing through the ear protection device determined by the sensor device.

In this way an ear protection system is provided to protect a patient during the imaging phase, such as Magnetic Resonance imaging MRI, where noise levels typically are around 95 to 105 dB and can be 130 dB and above. The wearing of ear protectors is mandatory for an MRI examination, however patients are generally not used to wearing such protection and consequently may not wear the ear protectors appropriately for the required level of protection, a situation exacerbated for children, elderly and patients with dementia. The provided system addresses this through e.g. monitoring the effectiveness of the protection being provided by the ear protection device, and giving supporting instructions to the patient.

According to an embodiment, the method may further comprise, preferably electronically and/or automatically, controlling a transition from the preparation phase to the imaging phase depending on the evaluation result. For example, the ear protection system may generate a signal or the like, to control a passage blocking device, such as a traffic light, a door, a barrier, or the like, to only be enabled or released if the ear protection is sufficient. This allows, for example, a high degree of automation in medical imaging and may also increase patient safety.

In an embodiment, the method may further comprise controlling, during the preparation phase, an actuator, the actuator being adapted to adjust the fit of the ear protection device around the ears of the patient, to apply a compression force that acts between the ear protection device and the patient to reduce the noise passing through the ear protection device, wherein, the instructions to the patient are omitted if the evaluation result indicates that a level of the noise passing through the ear protection device is below a certain threshold. In this way, generating unnecessary instructions may be omitted.

According to an embodiment, the actuator may be controlled based on scan information received from the medical imaging device. In this manner, pre-emptive levels of compression can be provided, for example when a next stage of scanning will be especially loud, signals from the scanner can be used to provide extra compression and a greater degree of attenuation is preparation for the loud sounds, thereby protecting the patient. When, the scanner is entering into a normal or quiescent mode, the ear muffs can be again correctly compressed in a not too tight manner, but also providing a safe level of sound attenuation, thereby providing for maximized comfort, with maximized safety for patients.

Additionally or alternatively, the method may further comprise controlling, during the preparation phase, an actuator, the actuator being adapted to adjust the fit of the ear protection device around the ears of the patient, to apply a compression force in one or more actuation intensities, wherein, if at one or more of the actuation intensities, the evaluation result indicates that the noise transmitted reaches or exceeds a certain threshold, further instructions to the patient are generated to refit or reposition the ear protection device. For example, the actuator may be controlled to move to an at least approximately maximum actuation intensity and/or an at least approximately minimum actuation intensity. After applying the one or more actuation intensities, it may be checked whether or not the seal of the ear protection device is still sufficient. If the actuator is able to break the seal by applying the one or more actuation intensities, the ear protections system may generate further instructions to refit or reposition, wherein these further instructions may be more specific as it is known at which actuation the seal is broken.

According to another aspect, there is provided a computer program element controlling one or more of the systems as previously described which, if the computer program element is executed by a processing unit, is adapted to perform one or more of the methods as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
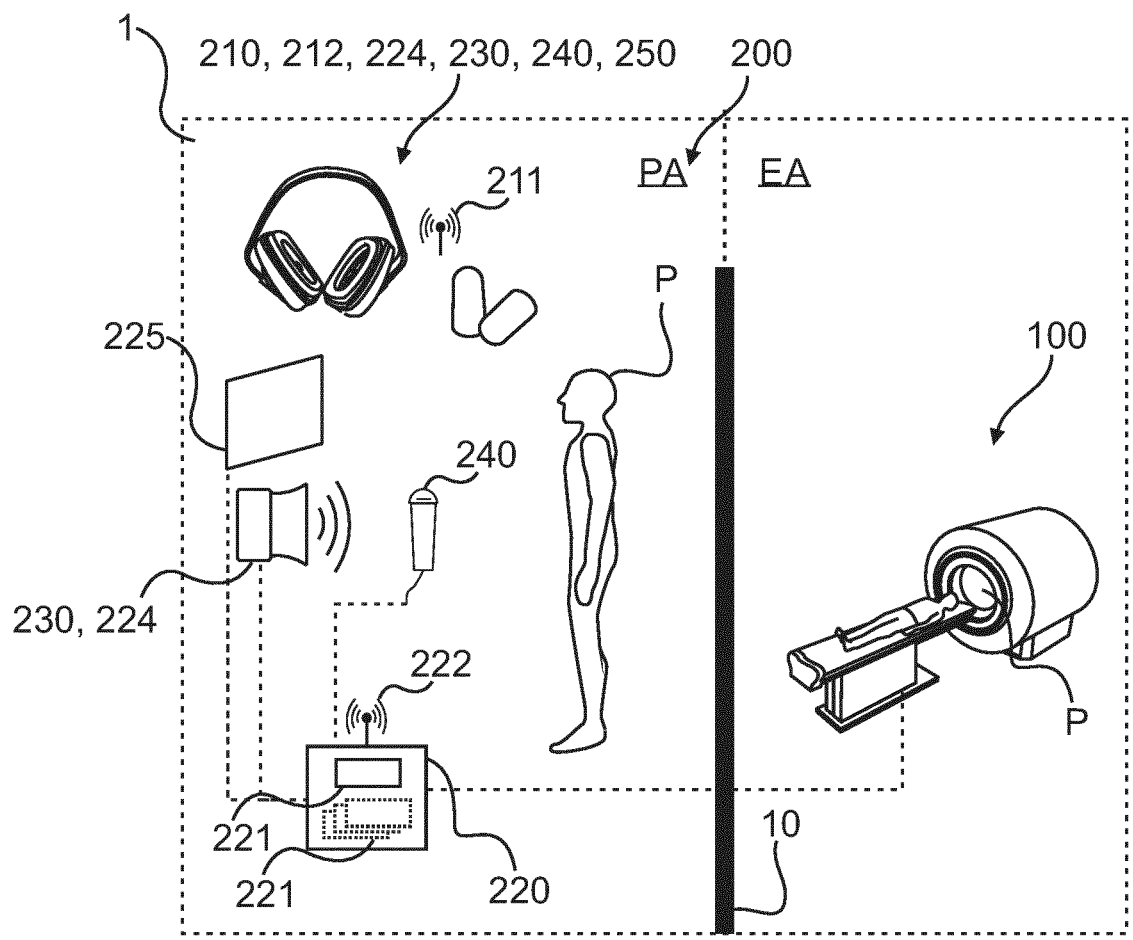
FIG. 1 shows in a schematic block diagram a medical imaging system according to an embodiment.

FIG. 1 shows in a schematic block diagram a medical imaging system 1, which is here based on MR imaging.

The medical imaging system 1 is adapted to be used for preparing and examining a patient P, and comprises a medical imaging device 100, such as an MR imaging device, and an ear protection system 200. It may be complemented that the ear protection system 200 could also be subsequently added to or integrated into an existing medical imaging system.

As indicated in FIG. 1 by a dashed line, there may be a first location PR where at least a part of the ear protection system 200 is located and a second location ER where the medical imaging device 100 is located. By way of example, the designation PA may refer to preparation area, and the designation EA may refer to examination area. Likewise, the operation or use of the medical imaging system 1 and/or the medical imaging device 100 and/or the ear protection system 200 may be differentiated into a preparation phase and an imaging phase, wherein in the preparation phase substantially the ear protection system 200 is used, and in the imaging phase the medical imaging device 100 is used, while the ear protection system 200 is still in use. In at least some embodiments, the first location PA and the second location EA may be physically or spatially separated from each other, wherein the medical imaging system 100 or the facility where the medical imaging system 100 is located may comprise a passage blocking device 10. This may comprise a physical device, such as a motor-driven door, or the like. Further, in at least some embodiments, the passage blocking device 10 may comprise a traffic light (not shown) or other visual and/or acoustic means adapted to indicate at least visually or acoustically whether or not the patient is to pass. The passage blocking device 10 may specifically be adapted to be electronically controlled by the medical imaging system 1 and/or the ear protection system 200.

The ear protection system 120, which can in at least some embodiments also be understood as a system that can be provided independently from the medical imaging device 100, comprises an ear protection device 210, adapted to be fitted around or in the ears of the patient P to be imaged. As indicated in FIG. 1, the ear protection device 210 may be configured or formed, for example, as a pair of ear muffs, ear plugs, or the like.

The ear protection device 210 comprises a first communication interface 211, which is here configured as a wireless communication interface, such as a Bluetooth module, Wi-Fi module, or the like. Further, the ear protection device 210 comprises at least one sensor device 212 adapted to determine a measurement of noise passing through the ear protection device towards the ears of the patient P. For example, the at least one sensor device 212 may comprise one or more of an optical sensor arrangement, an acoustic sensor arrangement such as one or more microphones, a pressure measuring arrangement to measure positive or negative air pressure within the ear muff, an electrical sensor arrangement., etc., which may also be combined. In an example, the at least one sensor device may comprise at least one microphone. The measurement of effectiveness of fit of the pair of ear muffs around the ears of the patient comprises at least one measured sound level. In an example, the at least one sensor device comprises a pair of air tubes. A first air tube of the pair of air tubes connects an inner chamber of a first ear muff that is configured to surround a first ear of the patient to the at least one microphone. A second air tube of the pair of air tubes connects an inner chamber of a second ear muff that is configured to surround a second ear of the patient to the at least one microphone. In other words, air tubes connect the inner portion of the ear muffs, to detect the level of noise to which the patient's ears are being subjected, to microphones that are external to the ear muffs, for example integrated into an in-room operating console of an MRI system, or integrated with the MRI head coil, or integrated with the patient support for example. In this manner, the wired microphones are at a safe distance from the patient and are safely outside of the imaging region of the MRI system, whilst passive air tubes are in that region transferring the level of sound at the patient's ears to these external microphones, where that level of sound indicates the effectiveness of fit of the ear protection device.

It was established that it is not always necessary to measure the sound level at the ear to assess the effectiveness of the ear protection, and this led to the development of the above discussed proxy methods, which are described in more detail below. Specifically, it has been established that the effectiveness of the acoustic protection provided by the ear muffs can be related to the quality of the seal between the ear muffs and the skin surrounding the patient's ear. The monitoring of this level of seal led to the different proxy methods to determine an effectiveness of fit that could be related to the acoustic attenuation.

Thus, as now described a series of proxy measurements can be used to assess the quality of this seal between the ear muffs and the patients and hence—indirectly—the effectiveness of the ear protection provided by the ear muffs. The proxy methods can take any of the following physical measurement approaches:

A light based approach in which the quality of the seal is assessed using a light leakage approach across the seal. For example in a simple approach a photosensitive device (like a photodiode) is added to the inside of the ear muff—which is ideally non-transparent. Any light leaking from the environment into the ear muff will be detected by the photosensor and is a direct indication of a poor seal—which in turn will reduce the effectiveness of the protection In a first electrical approach, two electrodes are added at the seal position to make contact with the patient's skin and the impedance/conductance between the electrodes is measured. The conductance/capacitance increases with the firmness of the contact of the electrodes with the skin, which can be used as an indication of good seal after a suitable calibration. Highly resistive wiring is used for the electrical set-up to ensure RF safety for this embodiment.

In a second electrical approach in which the quality of the seal is assessed using an electrical signal at the seal. A single thin film electrode is added close to the seal position, isolated from the patient's skin by a thin insulating layer. A measurement is then made of the capacitance against a common ground plane, i.e. the RF screen of the body coil. A reduction in capacitance results when the spacing of the electrode from the skin increases and is a direct indication of a poor seal—which in turn reduces the effectiveness of the protection. Highly resistive wiring is again used for the electrical set-up to ensure RF safety for this embodiment.

Further suitable electrical set-ups using one or more electrodes and measurement of mutual complex impedances between those may be used to determine whether ear protection devices (ear muffs, ear plugs) provide a tight seal.

Another approach is based on a slight constant positive or negative air pressure within the ear muff. Any loss of tight fit will result in a pressure drop, or if a feed-back loop is used to keep the pressure constant, into an increase of air supply to keep the pressure at preset level.

Because the ear is very susceptible to pressure differences, another approach is to use a different gas than air (nitrogen, carbon dioxide, argon) within the muffs at surrounding pressure and to measure the gas composition within the muff. Any ingress of air indicates a loss of a tight seal. Gas sensors are relatively inexpensive and can be selected such that they can be operated with highly resistive wiring to ensure RF safety.

Several of these approaches have advantages in the MR compatibility and simplicity of the physical principle compared to the direct measurement of the sound level.

In all of the above approaches, the measured effectiveness of fit of the ear muffs, directly determined from a sound level, or using the above proxy methods, can be used with the pneumatic (or other actuation) system to adjust the compression of the ear muffs to the patient's head to provide the correct, and comfortable, level of protection.

Further, the ear protection system 200 comprises a patient assistance device 220, adapted to generate and/or output suitable instructions to the patient P to assist the patient P to fit the ear protection device 210 in a proper way. The patient assistance device 220 may be any suitable kind of computer device or the like, comprising, for example, a data processing unit 223, a second communication interface 222 adapted to establish and/or provide a communication link to the first communication interface 211 of the ear protection device 210, and a number of function modules 223, which may be stored in a memory, may be executed by the data processing unit 221 and may be adapted to provide some or all of the functionalities described herein. Further, the patient assistance device 220 comprises at least one audio output device 224 adapted to provide the instructions of the patient assistant device 220 to the patient P in audio. For example, the audio output device 224 may be an external loudspeaker in e.g. the first location PA and/or a loudspeaker integrated into the ear protection device 210. Alternatively or additionally, the patient assistance device 220 comprises at least one graphical output device 225 arranged in e.g. the first location PA and adapted to provide the instructions of the patient assistant device 220 to the patient P visually. For example, the graphical output device 224 may comprise one or more of a display, a video screen, or the like.

Further, the ear protection system 200 comprises a controllable signal emitter 230 adapted to output a proxy signal representing an expected imaging device noise and to be measured by the at least one sensor device. By way of example, the signal emitter 230 may be configured or formed as a loudspeaker, a light emitter to emit light, a pressure generator to provide a slight constant positive or negative air pressure within the ear muff, an electrical signal representative of the contact between the ear protector and the skin of the patient. or the like. It may be controllable by the ear protection system 200 and/or the patient assistant device 220, wherein the signal output may be based on recorded or generated audio data, generated light, pressure, electrical signal etc.

Further, the ear protection system 200 comprises at least one microphone 240, adapted to capture sound from and/or the voice of the patient P. The microphone 240 may be arranged in the first location PA and/or may be integrated into the ear protection device 210.

As indicated in FIG. 1 by dashed lines, the entities described above may be interconnected to each other by suitable data lines, by a wireless communication link, or the like.

In general, during the preparation phase of the patient that precedes the imaging phase using the medical imaging device 100, the ear protection device 210 and the patient assistance device 220 are communicatively connected to each other via the first and second communication interface 211, 222, and the patient assistance device 210 generates assisting instructions to the patient depending on an evaluation of the generated noise and the measurement of noise passing through the ear protection device 210 determined by the sensor device 212.

Optionally, the ear protection system 200 may further comprise a natural language processing, NLP, engine, which may be implemented as e.g. a function module 221, adapted to affect the generation of the instructions at least based on the measurement of noise passing through the ear protection device 210 determined by the sensor device 212.

It is noted that the above may be carried out by using other sensor technologies, such as an optical sensor, where the NLP engine may be driven by the relationship of a light intensity to a certain light intensity threshold.

Further, the NLP engine may utilize Natural Language Understanding (NLU), adapted to understand questions or comments that the patient may make. For this purpose, the ear protection system may comprise an audio input device, such as the microphone 240. Further, optionally, the NLP engine may utilize Natural Language Generation (NLG), adapted to generate responses to the patient P based on e.g. the patient's P actions and requirements.

Optionally, the NLP engine may further be adapted to at least semi-automatically generate the instructions to the patient in speech based on the recording or capture from the microphone 240.

Further, the ear protection system 200 further comprises an actuator 250 (see also Fig. ?) adapted to adjust the fit of the ear protection device around the ears of the patient P by applying a compression force that acts between the ear protection device 210 and the patient P, wherein the patient assistant device 220 may further be adapted to generate instructions regarding the operation of the actuator 250. For example, the data processing device 221 may be configured to control the actuator 250 to adjust the fit of the pair of ear muffs around the ears of the patient, the control comprising utilization of the measurement of effectiveness of fit of the ear protection device. Optionally, the actuator 250 may be configured as a pneumatic system that is adapted to adjust the compression until a correctly tight seal is provided around the ear protection device 210.

Figure 2:
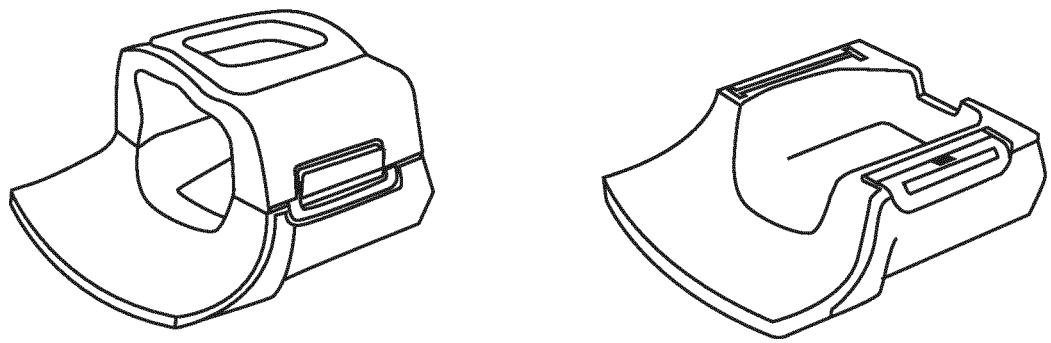
FIG. 2 shows an example of a MR head-coil consisting of a base part and top part, also showing the base part alone.

Referring now to FIG. 2, the ear muffs, similar to those shown in FIG. 1 but with pistons as part of a pneumatic system to change the level of compression provided around the head, are equipped with twin air tubes for use during an MRI scan or examination. The air tubes extend into the ear muff and have an opening on the ear side of the ear muffs, where sound is being attenuated. The air tubes are connected to loudspeakers in the MRI system to provide music or operator instructions to the patient. However, the air tunes are additionally connected to a pair of microphones in a part of the MR system, that separately measures the sound levels at both ears of the patient within the ear muffs. If appropriate high resistance circuitry is provided the microphones can be positioned within the ear muffs, in the attenuated region, but as the air tubes are provided for communication with the patient it has been found to be easier to use standard microphones that are external to the RF active part of the MRI device, and use those air tubes to relay sound to the microphones and this has been found to be a particularly advantageous embodiment. The microphones can be integrated into the communication unit of the MRI system that holds the loudspeakers used in connection with the MR ear muffs displayed. This can require long air tubes, which may introduce additional noise into the microphone system when moving the tubes. Therefore, the microphones can alternatively be integrated into the MR head coil (See FIG. 2). The air tubes coming from the ear muffs are connected by the staff to hose adapters integrated in the MR headcoil, which internally holds the microphones. The microphones may similarly be integrated with the patient support if necessary.

The air tubes can actually extend into the ear muffs, and then extend through ear plugs (similar to those shown in FIG. 1), where the patient has the ear plugs inserted into their ears. In this way, the sound level, indicative of an effectiveness of fit is measured at exactly the right position, adjacent to the ear canal. Indeed, the system can work without the ear muffs. Here. The air tunes extend through the ear plugs and to microphones, and sound levels picked up are sent to a data processing unit that provides an output if the sound level is too great. Thus, even if the patient wears only ear plugs without the ear muffs, an adaptive reaction to a too high in-ear sound level can be provided by issuing warnings and triggering a patient/staff action, or even by providing an automatic scan abort.

Figure 3:
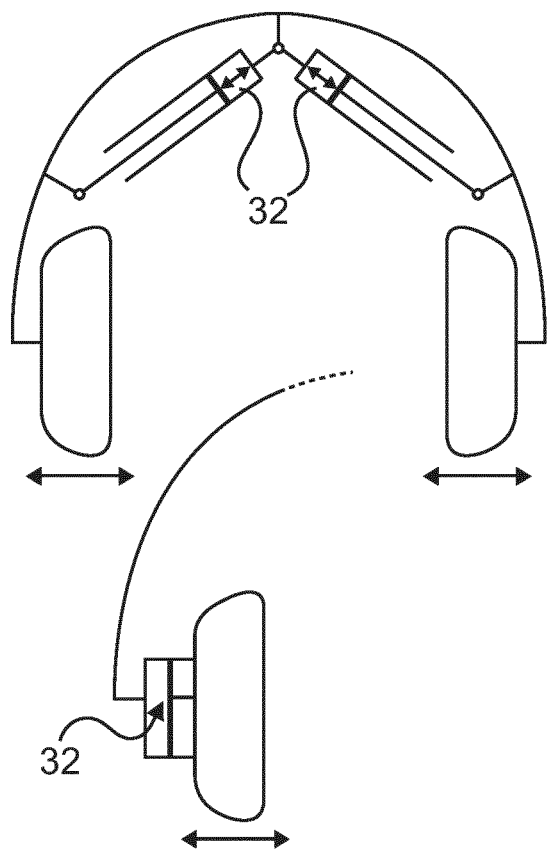
FIG. 3 shows examples of ear muffs of an adaptive ear protection system with a pneumatic system fed by pressurized air, showing in the example with two ear muffs an example of how increased air pressure can be used to decrease compression around the ears and showing in the example with one ear muff an example of how increased air pressure can be used to increase compression around the ear.

FIG. 3 shows the ear muffs, equipped with a pneumatic compression system, fed by pressurized air provided through an additional lumen in the connection tube. Thus, the connection tube or air tube is a tube with two lumina and as such is essential a compound tube consisting of two tubes. One tube is for the sound communication, and a second tube is for the pneumatic system. A software-controlled piston 32 integrated into the MR system connects to the second tube for the pneumatic system that connects to a second set of pistons in the ear muff.

Then, two pistons of the pneumatic compression system can be utilized with the main structure of the ear muffs, where increased air pressure decreases the compression of the muffs by pushing the two ear muffs away from each other, as shown in FIG. 1 where extension of the two pistons moves the ear muffs away from each other. Additionally, an additional piston associated with an ear muff can be used to move the ear muff away from the main structure in an inward direction, to compress both ear muffs against the patients head, with increased air pressure used to increases the compression of the muffs. This is shown in FIG. 3 with respect to the single ear muff shown, where the piston is adjacent to the ear muff. Thus, for compression there need only be one piston associated with one ear muff to compress both ear muffs. However, more complex relaxation and compression systems can be provided where the ear muffs can move independently due to a part of the main structure of the ear muffs being immobile with respect to the patient's head for example. Thus, the clamp or main structure of the MR ear muffs is provided with an air-pressure-actuated system to adjust the compression to the head of the patient. This avoids any wiring and active electrical devices that may interfere with the MR equipment, maintaining MR safety and image quality during scanning. Multiple embodiments are possible to realize the mechanics of the pneumatic system, as described above. They all have in common that a lumen in a tube of the ear muff provides pressurized air to some form of actuator 250 in the clamp. The pressurized air is provided by a software-controlled piston integrated in the MR system. The actuator associated with the second set of pistons can work against springs, thereby either releasing the ear muffs from the head or compressing them to the head of the patient. In even further embodiments the pneumatic system the air pressure may also be used to inflate a section of the contact pad which surrounds the ear of the patient. In such an actuator also the increase of pressure will result in a stronger seal of the ear muff to the patients head.

It was established that it is not always necessary to measure the sound level at the ear to assess the effectiveness of the ear protection, and this led to the development of the above discussed proxy methods, which are described in more detail below. Specifically, it has been established that the effectiveness of the acoustic protection provided by the ear muffs can be related to the quality of the seal between the ear muffs and the skin surrounding the patient's ear. The monitoring of this level of seal led to the different proxy methods to determine an effectiveness of fit that could be related to the acoustic attenuation.

Thus, as now described a series of proxy measurements can be used to assess the quality of this seal between the ear muffs and the patients and hence—indirectly—the effectiveness of the ear protection provided by the ear muffs. The proxy methods can take any of the following physical measurement approaches:

A light based approach in which the quality of the seal is assessed using a light leakage approach across the seal. For example in a simple approach a photosensitive device (like a photodiode) is added to the inside of the ear muff—which is ideally non-transparent. Any light leaking from the environment into the ear muff will be detected by the photosensor and is a direct indication of a poor seal—which in turn will reduce the effectiveness of the protection In a first electrical approach, two electrodes are added at the seal position to make contact with the patient's skin and the impedance/conductance between the electrodes is measured. The conductance/capacitance increases with the firmness of the contact of the electrodes with the skin, which can be used as an indication of good seal after a suitable calibration. Highly resistive wiring is used for the electrical set-up to ensure RF safety for this embodiment.

In a second electrical approach in which the quality of the seal is assessed using an electrical signal at the seal. A single thin film electrode is added close to the seal position, isolated from the patient's skin by a thin insulating layer. A measurement is then made of the capacitance against a common ground plane, i.e. the RF screen of the body coil. A reduction in capacitance results when the spacing of the electrode from the skin increases and is a direct indication of a poor seal—which in turn reduces the effectiveness of the protection. Highly resistive wiring is again used for the electrical set-up to ensure RF safety for this embodiment.

Further suitable electrical set-ups using one or more electrodes and measurement of mutual complex impedances between those may be used to determine whether ear protection devices (ear muffs, ear plugs) provide a tight seal.

Another approach is based on a slight constant positive or negative air pressure within the ear muff. Any loss of tight fit will result in a pressure drop, or if a feed-back loop is used to keep the pressure constant, into an increase of air supply to keep the pressure at preset level.

Because the ear is very susceptible to pressure differences, another approach is to use a different gas than air (nitrogen, carbon dioxide, argon) within the muffs at surrounding pressure and to measure the gas composition within the muff. Any ingress of air indicates a loss of a tight seal. Gas sensors are relatively inexpensive and can be selected such that they can be operated with highly resistive wiring to ensure RF safety.

Several of these approaches have advantages in the MR compatibility and simplicity of the physical principle compared to the direct measurement of the sound level.

In all of the above approaches, the measured effectiveness of fit of the ear muffs, directly determined from a sound level, or using the above proxy methods, can be used with the actuator 250 and/or pneumatic system to adjust the compression of the ear muffs to the patient's head to provide the correct, and comfortable, level of protection.

A control system or processing unit can measure the sound level with the above described microphones (or via one of the proxy methods) during scanning and compares it to a threshold that provides a safe sound level. If the sound level (either measured directly or determined from a level of the seal of the ear muffs from a proxy method in association with a calibration factor) is above the threshold, the system increases the compression of the ear muffs to achieve a better sealing of the ear muffs. Otherwise, the compression is released to a more comfortable level. The system can ask the patient manually to adjust the devices in the situation where the system measures insufficient protection even for maximum compression. The system may finally alert the radiographer if this does not help. The system can increase the compression during loud scans and release compression during silent periods to increase overall comfort. The control system can also increase the compression if it is determined from a proxy method that the ear muff seal is not tight enough, and need not use a threshold. Thus, for example once the ear muff is tight after compression, for example light tightness is provided, a further degree of tightness can be provided via further compression.

The above described ear protection systems and associated methods of ear protection have certain advantages, including that the methods avoid the use of a listening test to test the effectiveness of ear protection, which is subjective, costs time, and may not be performed consistently, e.g. due to time pressure or inability of the patient to comply. The method allows permanent control during the entire exam and immediate action to be undertaken. The method catches cases where patients remove the ear muff (or ear plugs) protection during scanning, or where the attenuation is lowering during the scan because of loss of tight fit of the devices.

High Resistance Circuitry

Reference is made above to high resistance circuitry, used for example in the above described proxy methods. These electrical embodiments can involve the measurement of some resistance across a certain part of the skin, which is typically in the range of 0.1-10 MOhm. Thus, the high resistance circuitry can relate to small skin patches and attached resistive wires with about 10k Ohm/m leading to a pre-amplifier several tens of cm away from the patient, which can be used safely and without affecting the resistance measurement. Such circuitry has been shown to be safe in MR under defined.

The above medical imaging system 1 and/or the patient assistance device 220 may be operated as described below.

For example, the patient P may receive the ear protection device 210 already in the first location PA to learn and to apply it properly. Then, the patient P may apply the ear protection device 210 in the first location PA and checks proper noise suppression, guided by the patient assistance device 220. Only if this evaluation is positive, the patient P may allowed to advance to the second location EA, e.g. through the passage blocking device 10, which may be controlled automatically. Then, optionally, noise suppression may be monitored continuously during MR scanning. Optionally, scanning may be interrupted or stopped automatically if noise suppression falls below a pre-defined threshold level, that is rated as insufficient.

Figure 4:
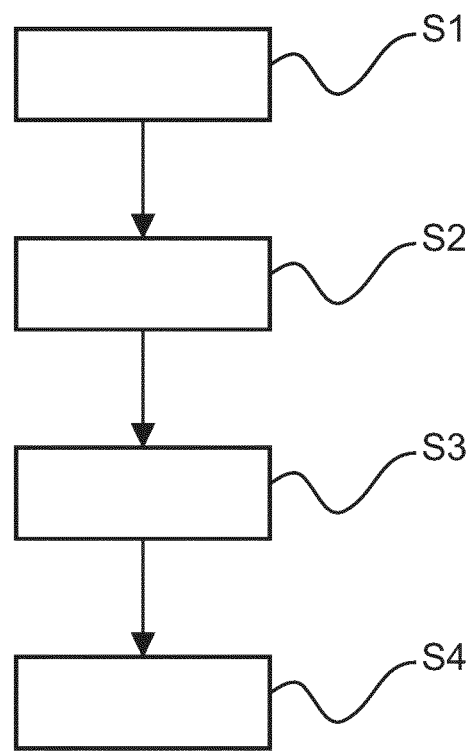
FIG. 4 shows a method of ear protection for a medical imaging device and/or in medical imaging.

FIG. 4 shows a, preferably computer-implemented, method of ear protection for a medical imaging device and/or in medical imaging.

In a step S1, the ear protection device 210, adapted to be fitted around or in the ears, to the patient p to be imaged, is provided.

In a step S2, the proxy signal is generated by the controllable signal emitter 230, during the preparation phase of the patient that precedes the imaging phase.

In a step S3, a measurement of noise passing through the ear protection device 210 towards the ears of the patient P is determined, by use of the at least one sensor device 212 measuring the proxy signal.

In a step S4, assisting instructions to the patient P depending on an evaluation of the generated noise and the measurement of noise passing through the ear protection device determined by the sensor device 212 is generated.

Optionally, during the preparation phase, the actuator 250 is controlled to apply a compression force that acts between the ear protection device 210 and the patient P to reduce the noise passing through the ear protection device 210. Thereby, the instructions to the patient P are omitted if the evaluation result indicates that a level of the noise passing through the ear protection device 210 is below a threshold.

Further optionally, during the preparation phase, the actuator 250 is controlled to apply a compression force in one or more actuation intensities, wherein, if at one or more of the actuation intensities, the evaluation result indicates that the noise transmitted reaches or exceeds a threshold, further instructions to the patient are generated to refit or reposition the ear protection device 210.

In another exemplary embodiment, a computer program or computer program element is provided that is characterized by being configured to execute the method steps of the method according to one of the preceding embodiments, on an appropriate system.

The computer program element might therefore be stored on a computer unit such as a smartphone, laptop, tablet, or a computer unit within an oral cleaning device such as a toothbrush, which might also be part of an embodiment. This computing unit may be configured to perform or induce performing of the steps of the method described above. Moreover, it may be configured to operate the components of the above described system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the interne or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that embodiments of the invention are described with reference to different subject-matter. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS 1 medical imaging system
10 passage blocking device
100 medical imaging device
200 ear protection system
210 ear protection device
211 first communication interface
212 sensor device
220 patient assistance device
221 data processing unit
222 second communication interface
223 function module
224 audio output device
225 graphical output device
230 noise source
240 microphone
250 actuator
EA examination area
PA preparation area
S1-Sx method steps

The invention claimed is:

1. An ear protection system for a medical imaging device, the ear protection system comprising:
   an ear protection device configured to fit around or in the ears of a patient (P) to be imaged, the ear protection device includes a first communication interface and at least one sensor device adapted to determine a measurement of noise passing through the ear protection device towards at least one of the ears of the patient,
   a controllable signal emitter, adapted to output a proxy signal representing an expected imaging device noise and to be measured by the at least one sensor device, a patient assistance device configured to assist the patient to fit the ear protection device by using one or more of a representation, communication and/or user interaction technique, and at least comprising a second communication interface, wherein, during a preparation phase of the patient preceding an imaging phase using the medical imaging device, the ear protection device and the patient assistance device are adapted to be communicatively connected to each other via the first and second communication interface, and the patient assistance device is adapted to generate and provide assisting instructions to the patient depending on an evaluation of the proxy signal and the measurement of noise passing through the ear protection device determined by the sensor device.

2. The ear protection system according to claim 1, wherein the ear protection system is adapted to provide a signal indicative of whether or not the preparation phase has been successfully completed to control a transition from the preparation phase to the imaging phase depending on the evaluation result.

3. The ear protection system according to claim 1 wherein the patient assistance device is further adapted to repeat the evaluation when it is determined based on the evaluation result that the noise being passed through reaches or exceeds a certain threshold, and to adapt the instructions to the evaluation result if necessary.

4. The ear protection system according to claim 1, wherein the ear protection system further comprises an actuator adapted to adjust the fit of the ear protection device around the ears of the patient by applying a compression force that acts between the ear protection device and the patient (P), and wherein the patient assistant device is further adapted to generate instructions regarding the operation of the actuator.

5. The ear protection system according to claim 1, wherein the ear protection system and/or the patient assistant device is further adapted to control a passage blocking device arranged between a first location where the preparation phase is carried out and a second location where the imaging phase using the medical imaging device is carried out, and wherein the passage blocking device is controlled to be released for the patient to pass when the evaluation result indicates that a level of the noise passing through the ear protection device is below a certain threshold.

6. The ear protection system according to claim 1, wherein the ear protection system and/or the ear protection device further comprises at least one audio output device adapted to provide the instructions of the patient assistant device to the patient in audio.

7. The ear protection system according to claim 1, wherein the ear protection system further comprises a natural language processing (NLP) engine adapted to affect the generation of the instructions at least based on the measurement of noise passing through the ear protection device determined by the sensor device.

8. The ear protection system according to claim 7, wherein the ear protection system further comprises at least one microphone adapted to capture the voice of the patient and/or the proxy signal, and wherein the NLP engine is further adapted to at least semi-automatically generate the instructions to the patient in speech based on the capture from the microphone.

9. The ear protection system according to claim 1, wherein the ear protection system further comprises at least two of the sensor devices adapted to determine a measurement of noise passing through the ear protection device towards the ears of the patient, and wherein at least one of the sensor devices is assigned to a first ear and at least one other of the sensor devices is assigned to a second ear of the patient.

10. A medical imaging system, comprising:
a medical imaging device, and
an ear protection system according to claim 1,
wherein, during a preparation phase of the patient preceding an imaging phase using the medical imaging device, the ear protection device and the patient assistance device are communicatively connected to each other via the first and second communication interface, and the patient assistance device generates instructions to the patient depending on an evaluation of the proxy signal and the measurement of noise passing through the ear protection device determined by the sensor device.

11. The medical imaging system according to claim 10, wherein, during the imaging phase, the noise passing through the ear protection device is monitored and evaluated, and when the evaluation indicates that a level of the noise passing through the ear protection device reaches or exceeds a certain threshold, the ear protection system is adapted to provide a signal indicative of whether or not the preparation phase has been successfully completed to control the imaging phase to be at least interrupted automatically by controlling the medical imaging device.

12. A computer program comprising executable instructions stored on a non-transitory computer readable memory for controlling a system according to claim 1, which when executed by a processor is configured to
generate (S2), by the controllable signal emitter, during a preparation phase of the patient preceding an imaging phase, a proxy signal representing an expected imaging device noise and to be measured by the at least one sensor device,
determining (S3), by use of the at least one sensor device, the measurement of noise passing through the ear protection device towards the ears of the patient; and
generate (S4) assisting instructions to the patient depending on an evaluation of the proxy signal and the measurement of noise passing through the ear protection device determined by the sensor device.

13. A method of ear protection in medical imaging, comprising:
providing an ear protection device, adapted to be fitted around or in the ears, to a patient to be imaged,
generating, by a controllable signal emitter, during a preparation phase of the patient preceding an imaging phase, a proxy signal representing an expected imaging device noise and to be measured by the at least one sensor device,
determining, by use of at least one sensor device, a measurement of noise passing through the ear protection device towards the ears of the patient,
generating assisting instructions to the patient depending on an evaluation of the proxy signal and the measurement of noise passing through the ear protection device determined by the sensor device.

14. The method according to claim 13, further comprising:
controlling, during the preparation phase, an actuator, the actuator being adapted to adjust the fit of the ear protection device around the ears of the patient (P), to apply a compression force that acts between the ear protection device and the patient to reduce the noise passing through the ear protection device,
wherein, the instructions to the patient are omitted if the evaluation result indicates that a level of the noise passing through the ear protection device is below a threshold.

15. The method according to claim 13, further comprising:
controlling, during the preparation phase, an actuator, the actuator being adapted to adjust the fit of the ear protection device around the ears of the patient, to apply a compression force in one or more actuation intensities,
wherein, if at one or more of the actuation intensities, the evaluation result indicates that the noise transmitted reaches or exceeds a threshold, further instructions to the patient are generated to refit or reposition the ear protection device.

* * * * *